United States Patent
Trenhaile et al.

(10) Patent No.: US 9,770,324 B2
(45) Date of Patent: *Sep. 26, 2017

(54) ARTHROSCOPIC BICEPS TENODESIS REPAIR

(71) Applicant: Smith & Nephew, Inc., Memphis, TN (US)

(72) Inventors: Scott Trenhaile, Belvidere, IL (US); Thomas C. May, Wrentham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/967,838

(22) Filed: Dec. 14, 2015

(65) Prior Publication Data

US 2016/0095693 A1 Apr. 7, 2016

Related U.S. Application Data (62) Division of application No. 12/427,978, filed on Apr. 22, 2009, now Pat. No. 9,241,783.

(60) Provisional application No. 61/053,127, filed on May 14, 2008.

(51) Int. Cl.
*A61F 2/08* (2006.01)
*A61B 17/86* (2006.01)
*A61B 17/04* (2006.01)

(52) U.S. Cl.
CPC .......... *A61F 2/0811* (2013.01); *A61F 2/0805* (2013.01); *A61B 2017/044* (2013.01); *A61B 2017/0445* (2013.01); *A61F 2002/0817* (2013.01); *A61F 2002/0829* (2013.01); *A61F 2002/0841* (2013.01); *A61F 2002/0852* (2013.01); *A61F 2002/0858* (2013.01); *A61F 2002/0888* (2013.01)

(58) Field of Classification Search
CPC .................. A61F 2/0805; A61F 2/0811; A61F 2002/0829; A61F 2002/0811
USPC ....... 606/304, 263, 264, 302, 301, 310, 314, 606/75

See application file for complete search history.

(56) References Cited

U.S. PATENT DOCUMENTS

| | | | | |
|---|---|---|---|---|
| 2,381,050 A | * | 8/1945 | Hardinge | A61B 17/742 411/55 |
| 4,462,395 A | * | 7/1984 | Johnson | A61B 17/00234 606/100 |
| 5,098,435 A | * | 3/1992 | Stednitz | A61B 17/1637 411/387.5 |
| 5,324,308 A | * | 6/1994 | Pierce | A61B 17/0401 606/232 |
| 5,456,685 A | * | 10/1995 | Huebner | A61B 17/8605 411/311 |
| 5,486,197 A | * | 1/1996 | Le | A61B 17/0401 411/355 |
| 5,643,264 A | * | 7/1997 | Sherman | A61B 17/7037 606/264 |

(Continued)

FOREIGN PATENT DOCUMENTS

FR 2622430 A1 * 5/1989 .......... A61B 17/686

*Primary Examiner* — Zade Coley
(74) *Attorney, Agent, or Firm* — Norman F. Hainer, Jr.

(57) ABSTRACT

The present disclosure relates to a fixation device. The fixation device includes a base portion having a first leg, a second leg, and a groove located between the first and second legs, and a top portion extending from the base portion. A method of tissue repair and a kit are also disclosed.

10 Claims, 8 Drawing Sheets

(56) References Cited

U.S. PATENT DOCUMENTS

| | | | | |
|---|---|---|---|---|
| 5,713,903 A * | 2/1998 | Sander | A61L 31/148 | 606/326 |
| 5,766,250 A * | 6/1998 | Chervitz | A61B 17/1675 | 606/232 |
| 5,782,865 A * | 7/1998 | Grotz | A61B 17/0401 | 606/104 |
| 6,524,317 B1 * | 2/2003 | Ritchart | A61B 17/0401 | 606/232 |
| 6,916,321 B2 * | 7/2005 | TenHuisen | A61B 17/8685 | 606/312 |
| 6,984,241 B2 * | 1/2006 | Lubbers | A61B 17/0401 | 606/103 |
| 7,517,357 B2 * | 4/2009 | Abrams | A61B 17/0401 | 606/232 |
| 7,572,283 B1 * | 8/2009 | Meridew | A61F 2/0805 | 606/232 |
| 7,678,134 B2 * | 3/2010 | Schmieding | A61B 17/0401 | 606/232 |
| 8,057,524 B2 * | 11/2011 | Meridew | A61F 2/0805 | 606/313 |
| 8,529,610 B2 * | 9/2013 | Graf | A61F 2/0811 | 606/304 |
| 8,790,368 B2 * | 7/2014 | Sullivan | A61B 17/0401 | 606/219 |
| 8,858,606 B2 * | 10/2014 | Graf | A61B 17/0401 | 606/304 |
| 9,060,748 B2 * | 6/2015 | Housman | A61B 17/0401 | |
| 9,259,307 B2 * | 2/2016 | Graf | A61B 17/0401 | |
| 2002/0147463 A1 * | 10/2002 | Martinek | A61B 17/0401 | 606/232 |
| 2004/0073233 A1 * | 4/2004 | Jannot | A61B 17/06061 | 606/148 |
| 2005/0080455 A1 * | 4/2005 | Schmieding | A61B 17/0401 | 606/232 |
| 2005/0177157 A1 * | 8/2005 | Jahng | A61B 17/3421 | 606/259 |
| 2005/0277923 A1 * | 12/2005 | Sweeney | A61B 17/1671 | 623/17.11 |
| 2006/0100630 A1 * | 5/2006 | West | A61B 17/0401 | 606/232 |
| 2007/0225719 A1 * | 9/2007 | Stone | A61B 17/0401 | 606/232 |

* cited by examiner

ARTHROSCOPIC BICEPS TENODESIS REPAIR

CROSS-REFERENCE TO RELATED APPLICATIONS

This application is a divisional of pending U.S. application Ser. No. 12/427,978, filed Apr. 22, 2009, which claimed the benefit of U.S. Provisional Application No. 61/053,127, filed May 14, 2008, all of which are incorporated by reference in their entireties.

BACKGROUND

Field of Technology

The present disclosure relates generally to arthroscopic biceps repair, and more specifically, devices and methods used for such repair.

Related Art

Current devices available for arthroscopic biceps tenodesis repair include suture anchors, metal post and washer screws, and interference screws. These devices provide immediate fixation of the tendon to the bone with little postoperative activity modification. However, the tendon must be delivered out of the body, stitched, and then re-inserted into a previously drilled bone hole. This reinsertion can be done through a portal, but is very technically demanding, precluding some patients from being a candidate for this procedure.

Therefore, a procedure is needed that is simple, reproducible, and that would allow both beginner and experienced surgeons to perform the procedure. Similarly, the devices used in the procedure would be simple to use, cost effective, and marketable to arthroscopic and open shoulder surgeons alike.

SUMMARY

In one aspect, the present disclosure relates to a fixation device. The fixation device includes a base portion having a first leg, a second leg, and a groove located between the first and second legs, and a top portion extending from the base portion. In an embodiment, the device is cannulated.

In another aspect, the present disclosure relates to a method of tissue repair including preparing a hole in a bone; placing soft tissue into the hole, via a fixation device, such that the soft tissue is located within a groove of the fixation device; and inserting an interference device into the hole.

In an embodiment, the fixation device includes a base portion having a first leg, a second leg, and the groove located between the legs, and a top portion extending from the base portion. In yet another embodiment, the method further includes applying tension to the soft tissue prior to inserting the interference device into the hole. In a further embodiment, inserting the interference device into the hole fixates the soft tissue to the bone. In yet a further embodiment, the interference device includes threads on an outer surface of the interference device.

In an embodiment, the interference device is configured for rotary advancement into the hole. In another embodiment, insertion of the interference device into the hole occurs via rotary advancement of the interference device into the hole. In yet another embodiment, the interference device includes a cannulation, the interference device coupled to the fixation device via disposal of the top portion within the cannulation. In a further embodiment, the method further includes removing the fixation device from the hole prior to inserting the interference device into the hole. In yet a further embodiment, the method further includes inserting a guide wire into the hole prior to inserting the interference device into the hole. In an embodiment, the method further includes inserting a guide wire into the hole after inserting the soft tissue into the hole via use of the fixation device. In another embodiment, the guide wire is inserted into the hole such that the guide wire is inserted through the fixation device, through the soft tissue, and into the bone.

In yet another aspect, the present disclosure relates to a kit. The kit includes a fixation device comprising a base portion including a first leg, a second leg, and a groove located between the first and second legs, and a top portion extending from the base portion; a guide wire; and a cannulated interference device including threads on an outer surface of the device. In an embodiment, the kit further includes a reamer and a delivery tool.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
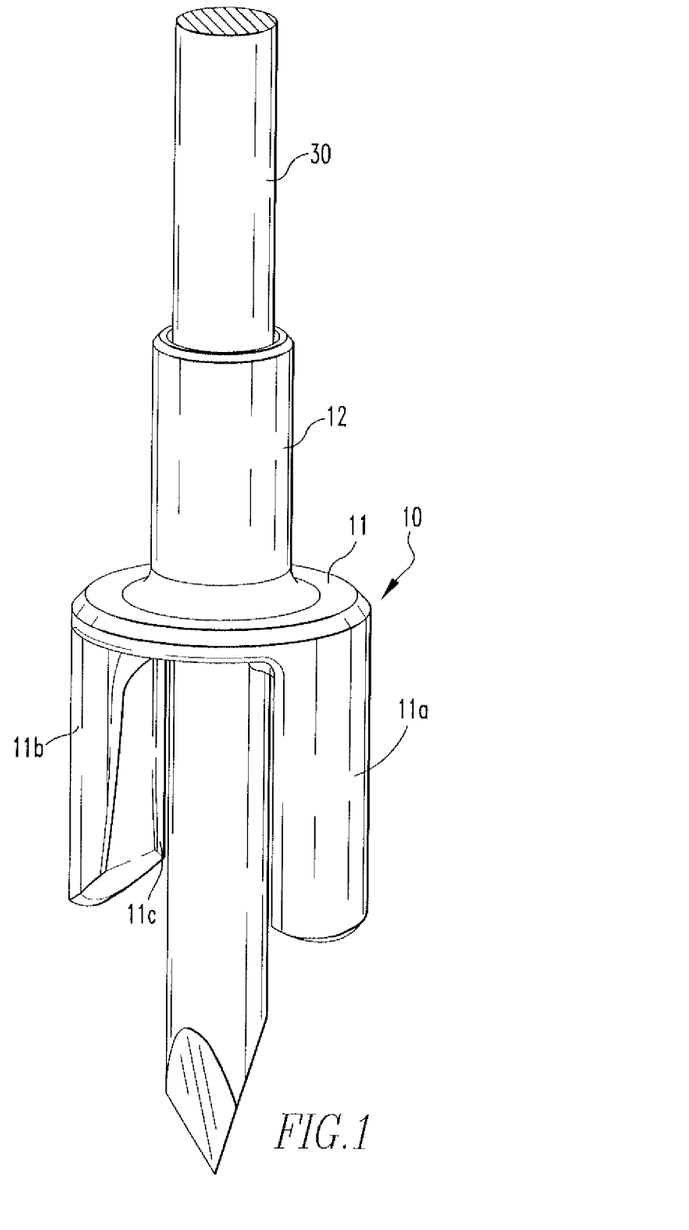
FIG. 1 shows a front view of the fixation device of the present disclosure.

FIG. 1 shows the fixation device 10 of the present disclosure. The device 10 is located on a guide wire 30 in preparation for delivery into a bone hole, as will be further described below. The device 10 includes a base portion 11 having a first leg 11a, a second leg 11b, and a groove 11c located between the legs 11a,11b. The device 10 also includes a top portion 12 extending from the base portion 11. As can be seen in FIG. 1, the top portion 12 has a smaller diameter than the base portion 11 and the device 10 is cannulated to allow passage of the guide wire 30. As will be further described below, the legs 11a,11b and the groove 11c cooperate to house soft tissue within the groove 11c and fixate the tissue within a bone hole. The top portion 12 of the device 10 may be a variety of lengths, thereby being longer or shorter than shown in FIG. 1.

Figure 2:
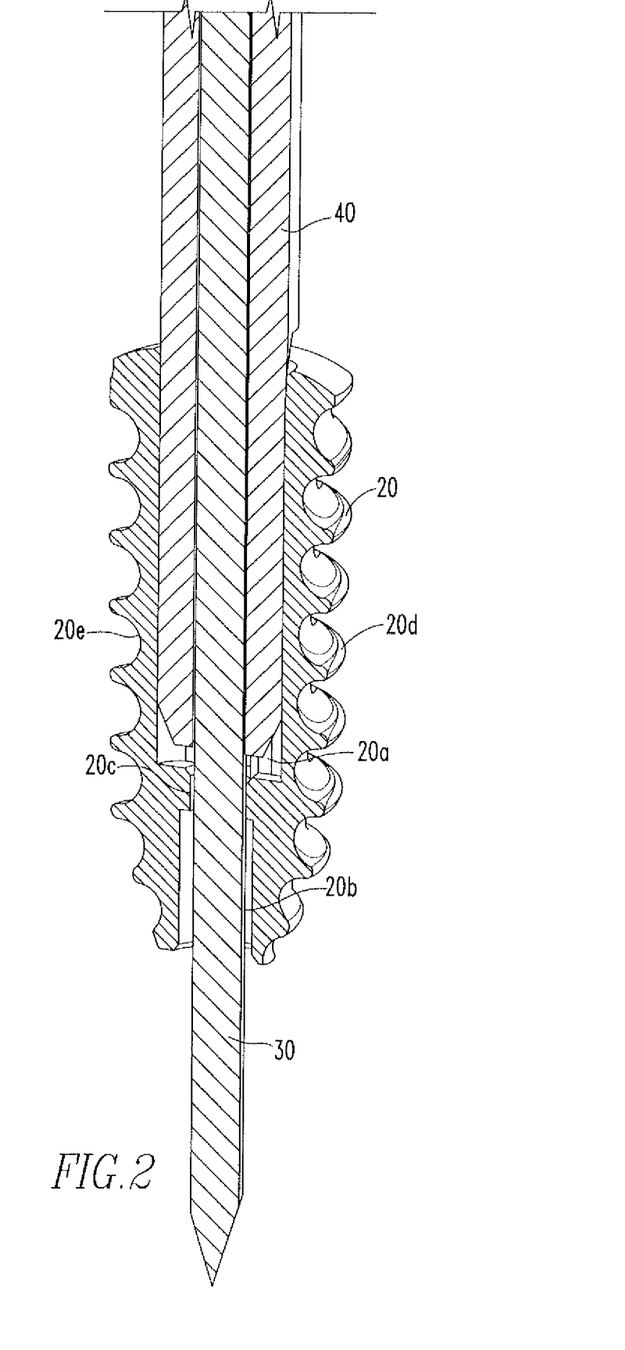
FIG. 2 shows a cross-sectional view of the interference device of the present disclosure.
Figure 3:
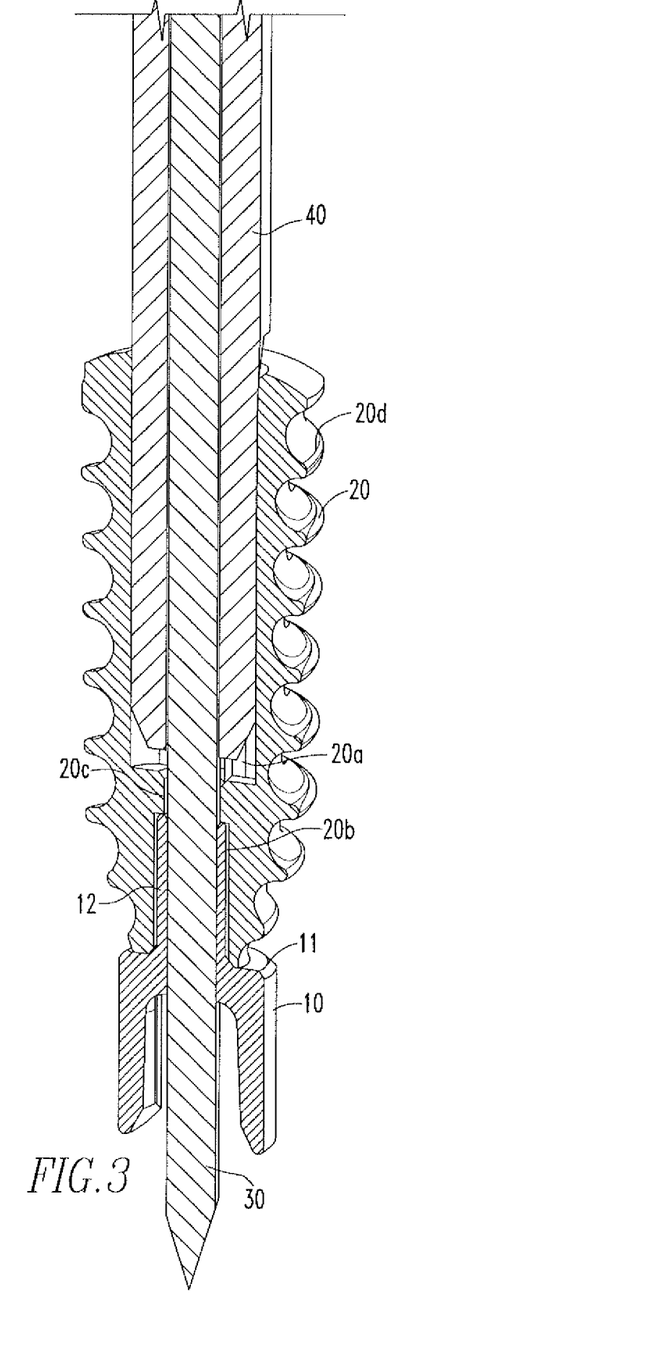
FIG. 3 shows a cross-sectional view of the tissue repair assembly of the present disclosure.
Figure 4:
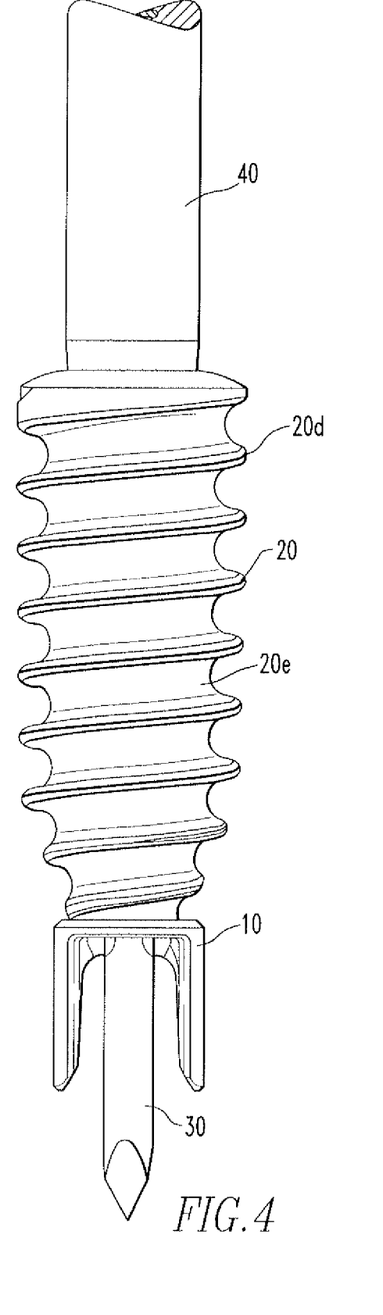
FIG. 4 shows a front view of the tissue repair assembly of the present disclosure.

FIG. 2 shows a cross-sectional view of the cannulated interference device 20 of the present disclosure. The device 20 is located on a guide wire 30 and is also engaged with a delivery tool 40 in preparation for delivery into a bone hole, as will be further described below. The device 20 includes a first cavity 20a, a second cavity 20b, and an area of reduced diameter 20c located between the cavities 20a,20b. The first cavity 20a is configured for engagement with the delivery tool 40 and, as can be seen in FIGS. 3 and 4, the second cavity 20b is configured for engagement with the top portion 12 of the fixation device 10. The delivery tool 40 is configured for insertion into the first cavity 20a and is cannulated for disposal of the tool 40 on the guide wire 30, as will be further described below. The device 20 also includes threads 20d on an outer surface 20e of the device 20. As will be further described below, the devices 10,20 cooperate to fixate soft tissue within a bone hole. The interference device 20 may include a cannulation without an area of reduced diameter, thereby not having two separate cavities.

Figure 5A:
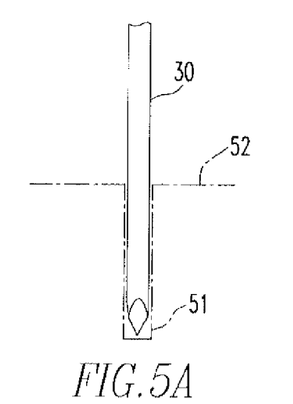
FIGS. 5A-5F show cross-sectional views of preparation of a bone hole during the method of tissue repair of the present disclosure.
Figure 5B:
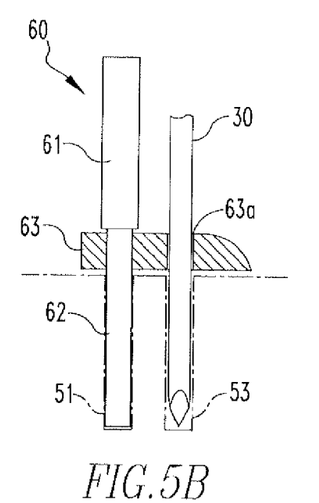
Figure 5C:
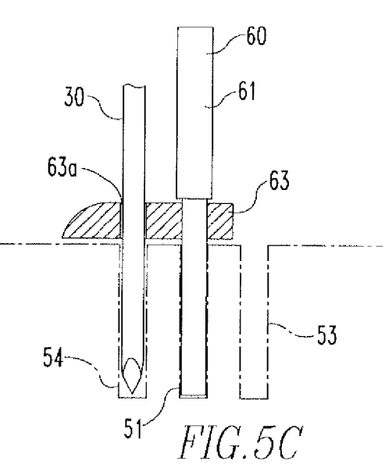

FIGS. 5A-5F show a method of preparing a bone hole during soft tissue repair 50. FIG. 5A shows the creation of a first groove 51 in a bone 52 via the use of the guide wire 30 shown above. After creation of the groove 51, the guide wire 30 is removed. FIG. 5B shows a drill guide 60 having a handle 61, a shaft 62, and an arm 63 located between the handle 61 and the shaft 62. The shaft 62 is inserted into the first groove 51 and the guide wire 30 is then inserted through an opening 63a on the arm 63 to create a second groove 53 in the bone 52. After creation of the second groove 53, the arm 63 is rotated about 180°, as shown in FIG. 5C, and the guide wire 30 is inserted through the opening 63a to create a third groove 54. The arm 63 may be coupled to the drill guide 60 in any manner that would allow the arm 63 to rotate relative to the shaft 62. Alternatively, the arm 63 may be coupled to the shaft 62 such that the arm 63 doesn't rotate relative to the shaft 62. Rather, the entire drill guide 60 is rotated in order to place the arm 63, and especially the opening 63a, in the proper position for creating the second groove 53.

Figure 5D:
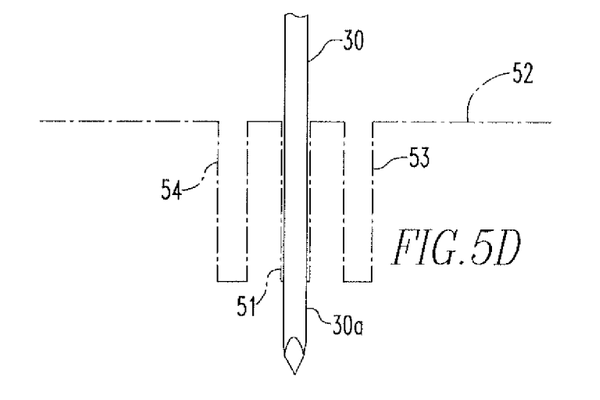
Figure 5E:
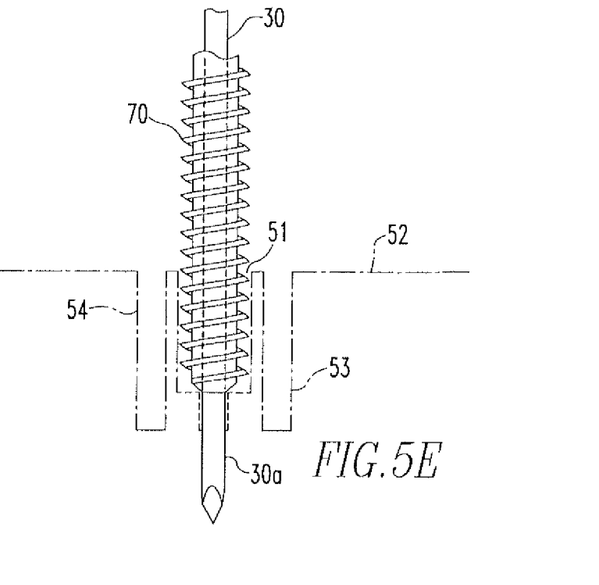
Figure 5F:
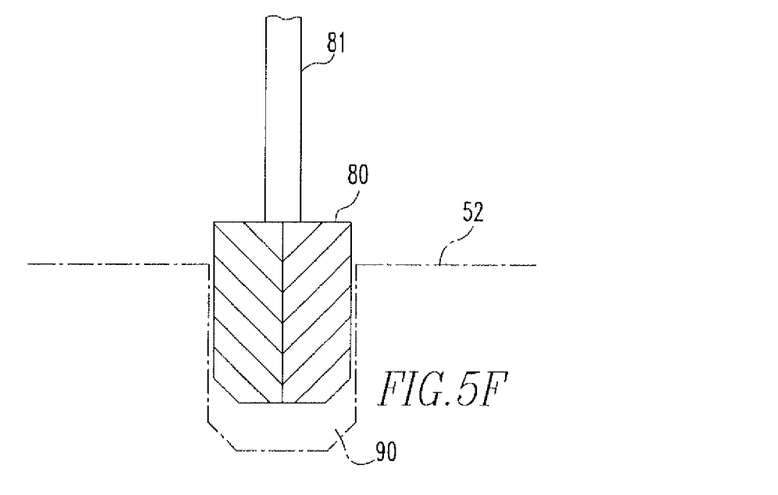

The drill guide 60 is subsequently removed from the groove 51 and the guide wire 30 is then re-inserted into the first groove 51, as shown in FIG. 5D, such that an end 30a of the wire 30 is inserted into the bone 52 lying beneath the groove 51. As shown in FIG. 5E, a cannulated reamer 70 is disposed on the guide wire 30 and inserted into the bone 52 to increase the diameter of the groove 51. For the purposes of this disclosure, the reamer 70 is between about 6 mm and about 8 mm in diameter. However, other diameters are within the scope of this disclosure. The reamer 70 and guide wire 30 are subsequently removed from the groove 51 and, as shown in FIG. 5F, a broach 80 is inserted into the bone 52 to further remove the remaining bone that is located between the first groove 51 and the second and third grooves 53,54, respectively, and to create the hole 90. The broach 80 includes a handle 81 coupled to the broach 80 for easier insertion of the broach 80 and removal of bone 52. After creation of the hole 90, the broach 80 is removed. Other methods of preparing a bone hole may also be used.

Figure 6A:
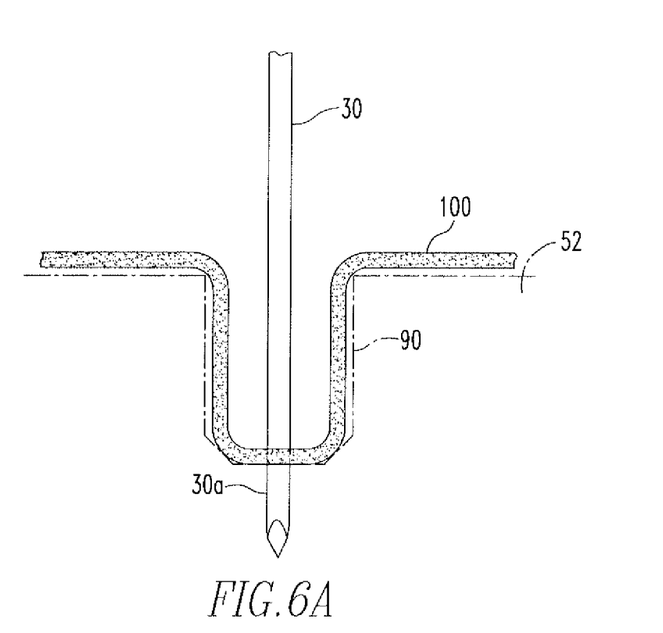
FIGS. 6A-6B show cross-sectional views of advancement of the fixation device and the soft tissue into the hole of FIGS. 5A-5F during the method of tissue repair of the present disclosure.
Figure 6B:
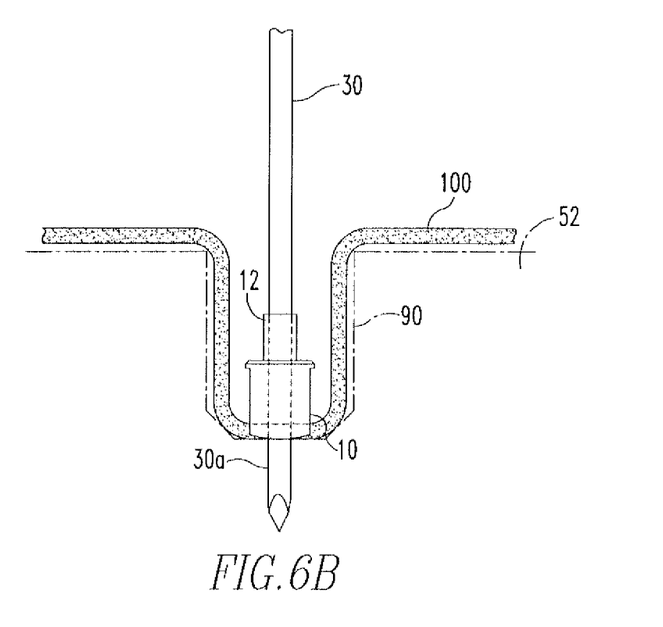

As shown is FIGS. 6A and 6B, soft tissue 100, such as a tendon or ligament, is subsequently placed over the hole 90. The guide wire 30 is used to engage and advance the tissue 100 into the hole 90. Advancement of the guide wire 30 is continued until the end 30a of the guide wire 30 is inserted into bone 52, as shown in FIG. 6A. The fixation device 10 is then disposed on the guide wire 30 and the wire 30 is used to engage the device 10 with the soft tissue 100, such that the tissue 100 is located within the groove 11c of the device 10, as shown in FIG. 6B.

Figure 7A:
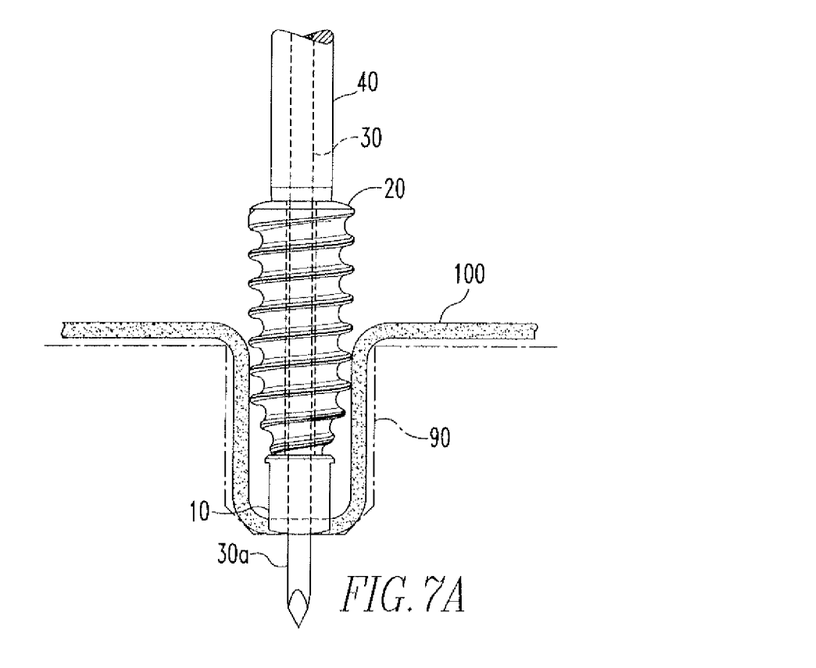
FIGS. 7A-7B show cross-sectional views of advancement of the interference device into the hole of FIGS. 5A-5F during the method of tissue repair of the present disclosure.
Figure 7B:
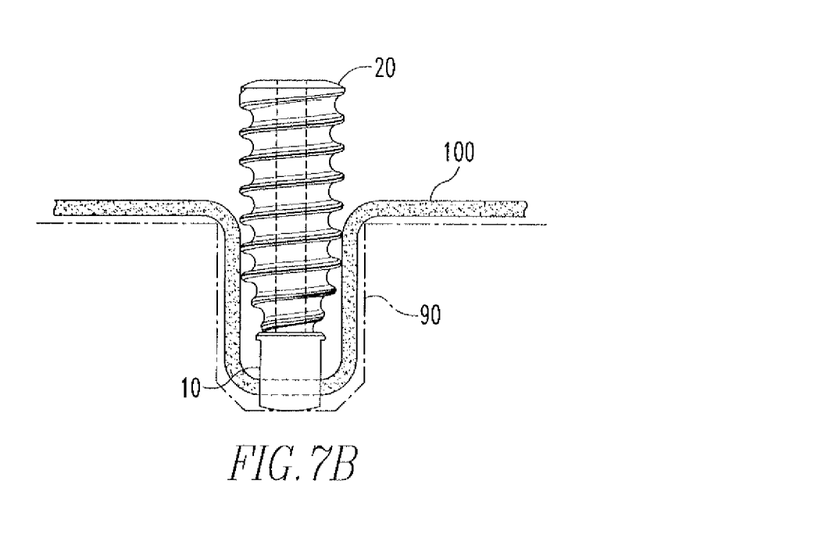

The interference device 20, shown above, is then coupled to the delivery tool 40 and the device 20/tool 40 assembly is then disposed over the guide wire 30 to insert the interference device 20 into the hole 90 via rotary advancement of the device 20, as shown in FIGS. 7A and 7B, and couple the interference device 20 to the fixation device 10, as described above. In FIGS. 7A and 7B, the top portion 12 of the fixation device 10 is disposed within the second cavity 20b and is therefore not shown. The guide wire 30 and the delivery tool 40 are subsequently removed from the hole 90 and the interference device 20. The interference device 20 is housed within the hole 90 such that the device 20 engages the tissue 100 and further fixates the tissue 100 within the hole 90. Prior to advancement of the device 20 into the hole 90, tension may be applied to the soft tissue 100.

Alternatively, it is possible to fixate the soft tissue 100 into the hole 90 in the following manner: placement of the soft tissue 100 into the hole 90 via use of the fixation device 10 such that the soft tissue 100 is located within the groove 11c and a downward force is applied to the fixation device 10 to drive the fixation device 10 and the soft tissue 100 into the hole 90; inserting the guide wire 30 through the fixation device 10, through the soft tissue 100, and into the bone 52; removing the fixation device 10 from the hole 90; inserting the interference device 20 into the hole 90 via use of the delivery tool 40 and the guide wire 30; and removal of the guide wire 30 and the delivery tool 40. In this manner, only the interference device 20 is used to fixate the tissue 100 to the bone 52, rather than both the fixation device 10 and the interference device 20, as described above with regards to FIGS. 6A and 6B. Prior to placement of the guide wire 30 into the hole 90, tension may be applied to the soft tissue 100.

For the purposes of this disclosure, the fixation device 10 and the interference device 20 are made from a resorbable polymer material. However, a metal material and other non-metal materials, either resorbable or non-resorbable, are also within the scope of this disclosure. In addition, the devices 10,20 may be made via a molding process or other process known to one of skill in the art. The cannulations and cavities 20a,20b may be formed during the molding process or after the molding process by drilling. Furthermore, rather than containing threads, the outer surface 20d of the device 20 may include other surface features that would allow engagement of the device 20 to the bone 90 and soft tissue 100. Also, the number of surface features may vary.

The depth of the grooves 51, 53, 54 and the hole 90 may vary based on surgeon preference or other factors known to those of skill in the art. The reamer 70 and broach 80 used may be any reamer 70 and broach 80 known to those of skill in the art. For the purposes of this disclosure, the method and devices, described above, are used in the arthroscopic repair of a biceps tendon, such that the tendon is reattached to the humeral bone. However, the method and devices may be used in the repair of other soft tissue.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of tissue repair comprising:
   preparing a hole in a bone;
   placing soft tissue into the hole via a guide wire, the guide wire inserted through the soft tissue and into the bone; followed by
   inserting a fixation device into the hole and over the soft tissue via use of the guide wire so that the soft tissue is located within a groove of the fixation device, the guide wire inserted through the fixation device; and
   inserting an interference device into the hole.

2. The method of claim 1 wherein the fixation device comprises a base portion including a first leg, a second leg, and the groove located between the legs, and a top portion extending from the base portion.

3. The method of claim 2 further comprising applying tension to the soft tissue prior to inserting the interference device into the hole.

4. The method of claim 2 wherein the interference device includes a cannulation, wherein the interference is device coupled to the fixation device via disposal of the top portion within the cannulation.

5. The method of claim 1 wherein inserting the interference device into the hole fixates the soft tissue to the bone.

6. The method of claim 1 wherein the interference device includes threads on an outer surface of the interference device.

7. The method of claim 1 wherein the interference device is configured for rotary advancement into the hole.

8. The method of claim 1 wherein insertion of the interference device into the hole occurs via rotary advancement of the interference device into the hole.

9. The method of claim 1 further comprising inserting the guide wire into the hole prior to inserting the interference device into the hole.

10. A method of tissue repair comprising:
    preparing a hole in a bone;
    anchoring soft tissue with the bone via a guide wire, the guide wire inserted through the soft tissue and into the bone;
    inserting a fixation device into the hole via use of the guide wire after the step of anchoring the soft tissue with the bone such that the soft tissue is located within a groove of the fixation device, the guide wire inserted through the fixation device; and
    inserting an interference device into the hole.

* * * * *